Figure 1:
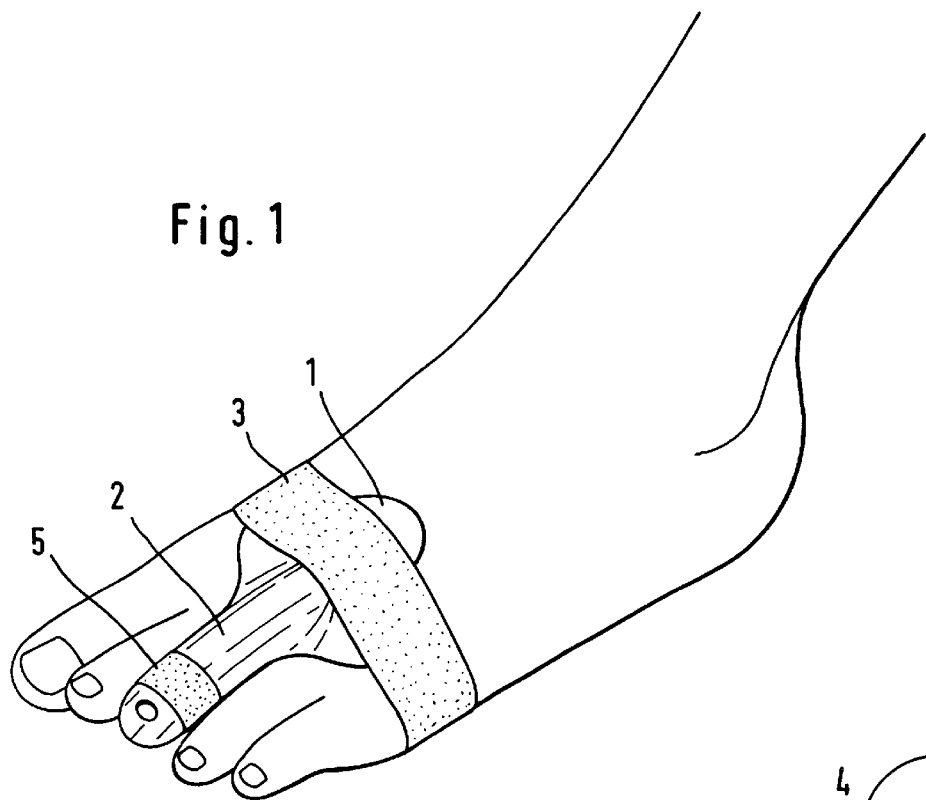

__

United States Patent [19]

Lockhart

[11] Patent Number: 5,769,805
[45] Date of Patent: Jun. 23, 1998

[54] TOE SPLINT FOR A MIDDLE TOE

[75] Inventor: Robert D. Lockhart, Sunnyvale, Calif.

[73] Assignee: Waldemar Link (GmbH & Co.), Hamburg, Germany

[21] Appl. No.: 766,968

[22] Filed: Dec. 16, 1996

[30] Foreign Application Priority Data

Sep. 19, 1996 [DE] Germany .................. 296 16 346.5

[51] Int. Cl.⁶ ........................................ A61F 5/00
[52] U.S. Cl. ............................................... 602/30
[58] Field of Search ................. 602/5–8, 11, 22, 602/30, 31; 128/880, 889, 892–893

[56] References Cited

U.S. PATENT DOCUMENTS

| | | | |
|---|---|---|---|
| 2,237,251 | 4/1941 | Longfellow | 602/22 |
| 2,523,606 | 9/1950 | Young | 602/7 |
| 2,617,413 | 11/1952 | Belknap | 128/880 |
| 2,818,062 | 12/1957 | Braxton | 602/30 |
| 2,835,248 | 5/1958 | Scholl | 602/30 |
| 2,920,621 | 1/1960 | Fettig | 602/31 |
| 3,211,142 | 10/1965 | Neu | 602/30 |
| 5,154,692 | 10/1992 | Lockhart | 602/5 X |

FOREIGN PATENT DOCUMENTS

| | | | |
|---|---|---|---|
| 602101 | 8/1934 | Germany | 602/30 |
| 2916894 | 11/1980 | Germany | 602/30 |

*Primary Examiner*—Linda C. Dvorak

[57] ABSTRACT

The invention relates to a toe splint for a middle toe, comprising a rear holding part to be placed against the metatarsus and a front supporting part which is to be placed onto the toe to be supported and the front end of which lies roughly in alignment with the holding part. The improvement according to the invention lies in the fact that the middle and/or rear part of the supporting part is arranged substantially higher than its front end.

8 Claims, 1 Drawing Sheet

TOE SPLINT FOR A MIDDLE TOE

The invention relates to a toe splint for one of the three middle toes, comprising a rear holding part to be placed against the metatarsus and a front supporting part which is to be placed onto the toe to be supported and the front end of which lies roughly in alignment with the holding part.

In a known toe splint of this type (U.S. Pat. No. 5,154,692), the holding part and the supporting part are mutually aligned throughout their length. Although this roughly corresponds to the natural toe setting relative to the metatarsus, problems can arise in cases of toe deformations.

The invention avoids this drawback by virtue of a higher arrangement of the rear part of the supporting part. In particular, it is high-arched, so that the supporting part runs in a convex curve. Its rear part is expediently raised by 7 to 15 mm relative to the line of alignment of the holding part. Particularly good variability of application and good rigidity is achieved if the transition from the supporting part to the holding part lies behind the remaining front edge of the holding part.

The invention is based upon the recognition that in most cases the sought-after supporting effect is merely dependent upon the foremost phalanx being fixed. For the rear phalanx and the region of the joints, the splint according to the invention offers adequate space. If, exceptionally, the rear phalanx has also to be immobilized by direct connection to the splint, sufficient contact can be achieved by providing the splint with additional padding.

Figure 2:
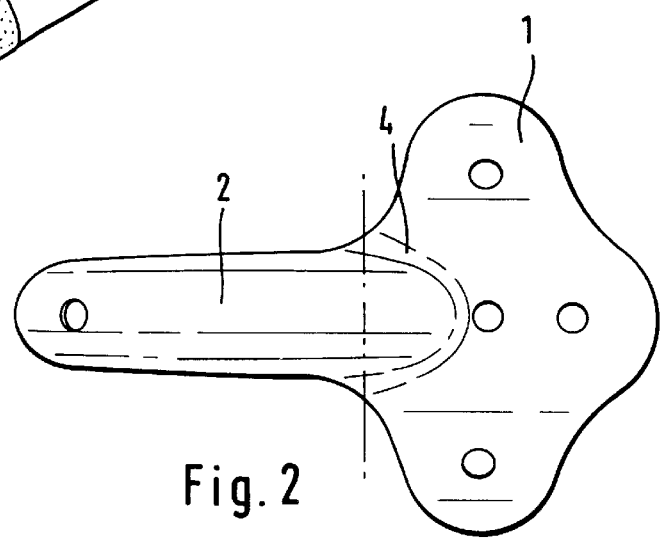
Figure 3:
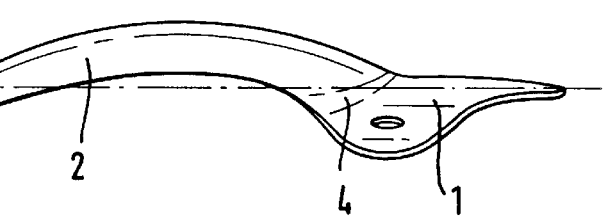
Figure 4:
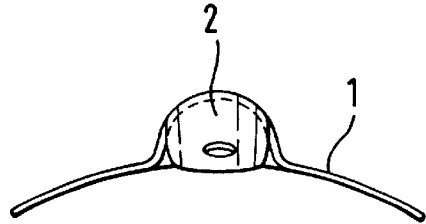

The invention is explained in greater detail below with reference to the drawing depicting an advantageous illustrative embodiment, in which:

FIG. 1 shows a foot with toe splint attached thereto,
FIG. 2 shows a top view,
FIG. 3 shows a side view and
FIG. 4 shows a front view of the toe splint.

The toe splint comprises a rear holding part 1 and a front supporting part 2. The holding part is constructed substantially flat and only slightly arched. It is wide, namely around 3–4 times as wide as one of the middle toes, and its length is not substantially less than its width. By means of an adhesive tape 3, it can be fastened in a fixed position on the back of the metatarsus. Adjoining in the middle towards the front is the supporting part 2, the width of which roughly corresponds to that of one of the three middle toes. Its length too roughly corresponds to the toe length. In cross-section it is curved to match the toe shape, its side margins running out at 30°–60° to the vertical. The front end of the supporting part lies roughly level with the line of alignment of the holding part 1, indicated by dash-dot lines. In contrast to the above, the middle and rear portion of the supporting part 2 is substantially raised relative to this line.

Furthermore, the supporting part 2 terminates at the rear not at the front limit line of the holding part 1, which limit line is indicated in dash-dot representation in FIG. 2 and roughly corresponds to the front boundary of the metatarsus, but is taken in its high-arched shape far into the flat holding part 1. The arc-shaped throat 4 denotes the transition from the high-arched supporting part into the holding part. Additional space is thereby created above the metatarsophalangeal joint in order to spare the extensor-tendon region. A very stable connection of the supporting part to the holding part is also obtained. This shape allows the splint to be moulded from a relatively thin, flexible plastics material, for example from roughly 1.5 mm thick polystyrene of a hardness equivalent to strong cardboard. The splint is thereby capable of yielding, particularly in the region of the flat holding part 1. Wearing comfort is thereby improved without adverse effect upon holding security.

The distal phalanx is generally fixed to the supporting part 2 using adhesive tape 5. The toe splint is expediently provided with a padding made from felt or the like, which padding is not represented in the drawing. The toe splint expediently consists of a thermoplastic material, which can be remoulded at comfortably manageable temperatures (particularly 50° to 80° C., preferably 60° to 70° C.).

I claim:

1. A toe splint for a middle toe, comprising:
   i) a rear holding part to be positioned upon dorsal the metatarsus; and
   ii) a front supporting part to be placed on top of the toe to be supported, said front supporting part comprising a front portion lying in general alignment with and approximately level with said rear holding part, and a raised arched middle part said raised arch middle part being curved in cross section to match the shape of the toe being splinted, and a rear part connecting said front supporting part to said rear holding part at a transition region, said transition region comprising an elevated arched throat.

2. The toe splint of claim 1, wherein, said middle part is raised by approximately 7–15 mm relative to said rear holding part.

3. The toe splint of claim 1, wherein said rear holding part is substantially flat.

4. A method, comprising:
   a) providing:
      i) a splint comprising a rear holding part and a front supporting part, said front supporting part comprising a front portion lying in general alignment with and approximately level with said rear holding part, and a raised arched middle part said raised arch middle part being curved in cross section to match the shape of the toe being splinted, and a rear part connecting said front supporting part to said rear holding part at a transition region, said transition region comprising an elevated arched throat; and
      ii) a patient having an injured toe; and
   b) positioning said rear holding part of said splint upon dorsal the metatarsus of said patient and placing said front supporting part onto the top of said injured toe.

5. The toe splint of claim 4, wherein, said middle part is raised by approximately 7–15 mm relative to said rear holding part.

6. The toe splint of claim 4, wherein said front supporting part has a width approximately corresponding with the width of one of the three middle toes.

7. The toe splint of claim 4, wherein said rear holding part is substantially flat.

8. The toe splint of claim 7, wherein said rear holding part has a width approximately corresponding to between approximately three and four times the width of one of the middle toes.

* * * * *